(12) United States Patent
Freelander

(10) Patent No.: US 12,036,361 B2
(45) Date of Patent: Jul. 16, 2024

(54) SYSTEM AND METHOD FOR A VAPORIZER

(71) Applicant: Freelander Innovations USA, LLC, Springfield, MO (US)

(72) Inventor: Michael Freelander, Springfield, MO (US)

(73) Assignee: Freelander Innovations USA, LLC, Springfield, MO (US)

( * ) Notice: Subject to any disclaimer, the term of this patent is extended or adjusted under 35 U.S.C. 154(b) by 165 days.

(21) Appl. No.: 17/494,551

(22) Filed: Oct. 5, 2021

(65) Prior Publication Data

US 2022/0023554 A1  Jan. 27, 2022

Related U.S. Application Data

(63) Continuation of application No. 16/703,459, filed on Dec. 4, 2019, now Pat. No. 11,167,099, which is a
(Continued)

(51) Int. Cl.
*A61M 15/06* (2006.01)
*A24F 40/30* (2020.01)
(Continued)

(52) U.S. Cl.
CPC ............ *A61M 15/06* (2013.01); *A24F 40/30* (2020.01); *A24F 40/40* (2020.01); *A24F 40/50* (2020.01); *A24F 40/60* (2020.01); *A61M 11/042* (2014.02); *A61M 15/0023* (2014.02); *A61M 15/0051* (2014.02); *A61M 15/008* (2014.02); *A24F 40/20* (2020.01); *A61M 2016/0021* (2013.01); *A61M 2205/3306* (2013.01); *A61M 2205/3334* (2013.01); *A61M 2205/3368* (2013.01); *A61M 2205/3553* (2013.01); *A61M 2205/3569* (2013.01); *A61M 2205/3584* (2013.01); *A61M 2205/3592* (2013.01); *A61M 2205/3653* (2013.01); *A61M 2205/368* (2013.01); *A61M 2205/505* (2013.01); *A61M 2205/52* (2013.01); *A61M 2205/8206* (2013.01); *A61M 2209/06* (2013.01)

(58) Field of Classification Search
CPC .......................... A61M 15/06; A61M 11/042; A61M 15/0023; A61M 15/0051; A61M 15/008; A61M 2016/0021; A61M 2205/3306; A61M 2205/3334; A61M 2205/3368; A61M 2205/3553; A24F 40/30; A24F 40/40; A24F 40/50; A24F 40/60; A24F 40/20
See application file for complete search history.

(56) References Cited

U.S. PATENT DOCUMENTS 9,706,944 B2 * 7/2017 Adamo ................ A61K 9/0075
9,820,510 B2 * 11/2017 Thomas, Jr. ............ A24F 40/46
(Continued)

*Primary Examiner* — Travis S Chambers
(74) *Attorney, Agent, or Firm* — Husch Blackwell LLP

(57) ABSTRACT

A method for controlling a vaporizer device may include determining a first temperature, vaporizing an inhalable substance at the first temperature, raising the first temperature by a temperature quantity, wherein a second temperature is a sum of the temperature quantity and the first temperature; and vaporizing the inhalable substance at the second temperature, wherein the temperature quantity is less than 3° C.

17 Claims, 14 Drawing Sheets

Related U.S. Application Data continuation of application No. 15/438,094, filed on Feb. 21, 2017, now Pat. No. 10,506,829.

(60) Provisional application No. 62/300,506, filed on Feb. 26, 2016.

(51) Int. Cl.
| | |
|---|---|
| *A24F 40/40* | (2020.01) |
| *A24F 40/50* | (2020.01) |
| *A24F 40/60* | (2020.01) |
| *A61M 11/04* | (2006.01) |
| *A61M 15/00* | (2006.01) |
| *A24F 40/20* | (2020.01) |
| *A61M 16/00* | (2006.01) |

(56) References Cited

U.S. PATENT DOCUMENTS

| | | | | |
|---|---|---|---|---|
| 10,471,223 | B2* | 11/2019 | Bourque | A61M 15/0043 |
| 2006/0102175 | A1* | 5/2006 | Nelson | A61M 15/0083 |
| | | | | 128/200.24 |
| 2009/0241949 | A1* | 10/2009 | Smutney | A61M 15/0023 |
| | | | | 128/203.15 |
| 2012/0255546 | A1* | 10/2012 | Goetz | A61M 11/042 |
| | | | | 128/202.21 |
| 2014/0053832 | A1* | 2/2014 | Postma | A24F 42/60 |
| | | | | 128/202.21 |
| 2015/0053217 | A1* | 2/2015 | Steingraber | A24F 40/50 |
| | | | | 131/329 |
| 2017/0027223 | A1* | 2/2017 | Eksouzian | A24F 40/60 |

* cited by examiner

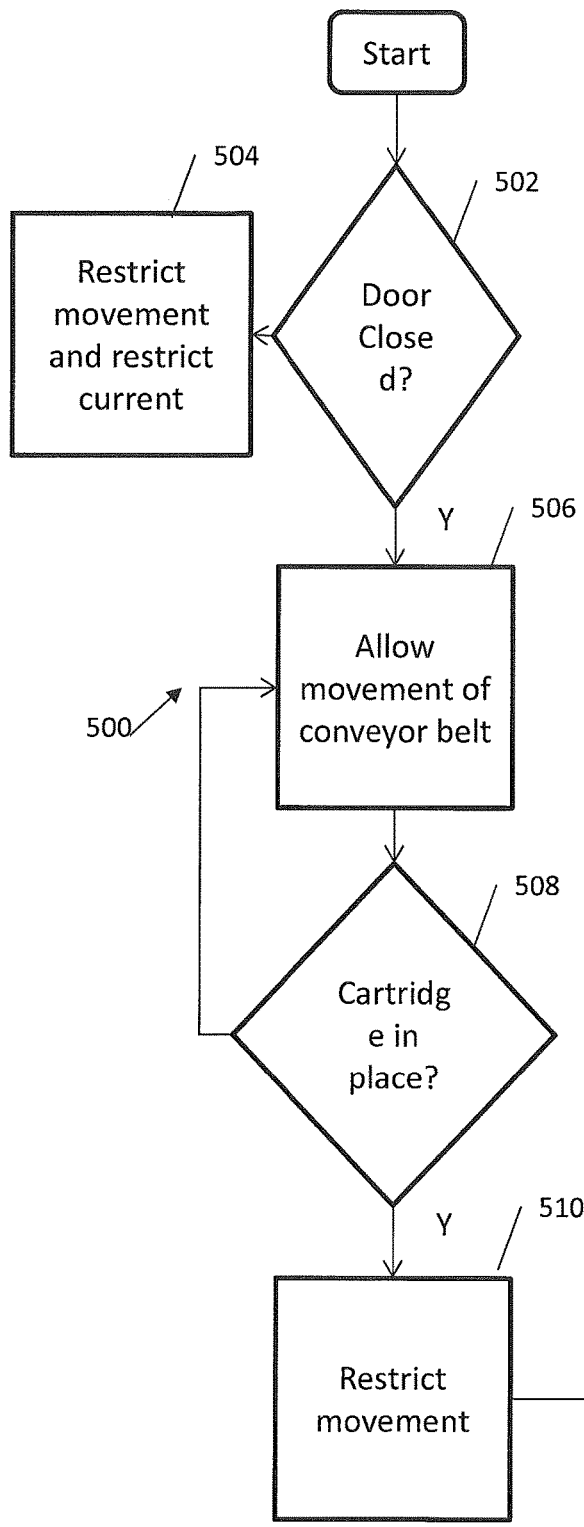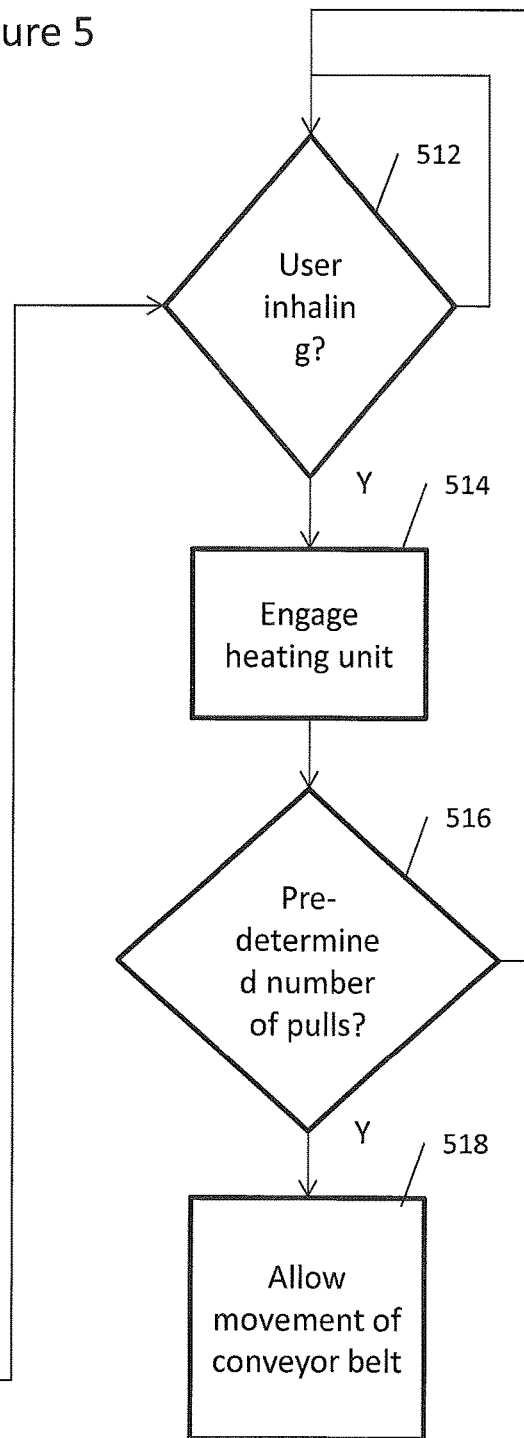
Figure 5

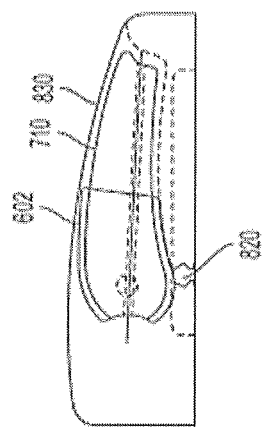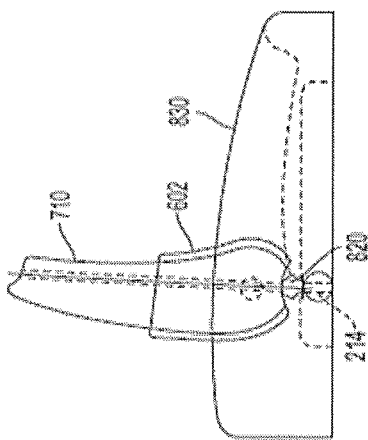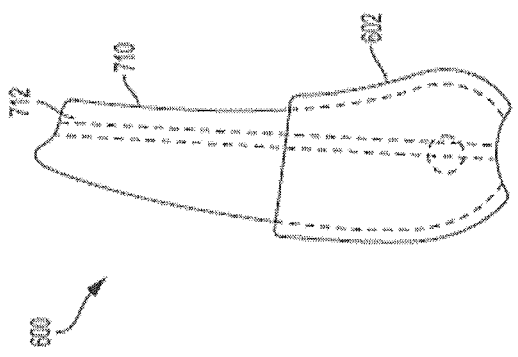

SYSTEM AND METHOD FOR A VAPORIZER

CROSS-REFERENCE TO RELATED APPLICATIONS

This application is a continuation of and claims priority to U.S. patent application Ser. No. 16/703,459 filed Dec. 4, 2019 and titled "System and Method for a Vaporizer" and U.S. patent application Ser. No. 15/439,094 filed Feb. 21, 2017 and titled "System and Method fora Vaporizer". U.S. patent application Ser. No. 16/703,459 and U.S. application Ser. No. 15/439,094 are hereby incorporated by reference.

FIELD

The present invention relates generally to vaporizers and inhalers.

BACKGROUND

Inhalers and vaporizers are conventionally used for medicinal and recreational purposes to deliver an inhalable substance in a gaseous form to a user. Vaporizers have been used recreationally with the use of recreational substances such as tobacco, hookah, and cannabis. Meanwhile, rescue inhalers have been used by people who have asthma or for other medical uses. Furthermore, some medicine may be delivered by an inhaler for the treatment of some respiratory diseases.

Generally, vaporizers, hookahs, electronic hookahs, and so-called "e-cigarettes" vaporize an inhalable substance via an electronic heater. The inhalable substance is inserted into the vaporizing unit by numerous means. However, the inhalable substance must be frequently refilled, which can be frustrating for users seeking to enjoy or benefit from the inhaled substance. Thus, there is a need in the art for a method, system, or device for convenient replacement of the inhalable substance into a vaporizer.

BRIEF DESCRIPTION OF THE DRAWINGS

FIG. 5 illustrates a method for moving a conveyer belt included within the vaporizer device.

FIGS. 8A, 8B, and 8C illustrate the mouthpiece portion and mouthpiece base connected to the vaporizer device according to an exemplary embodiment.

DETAILED DESCRIPTION

Figure 1A:
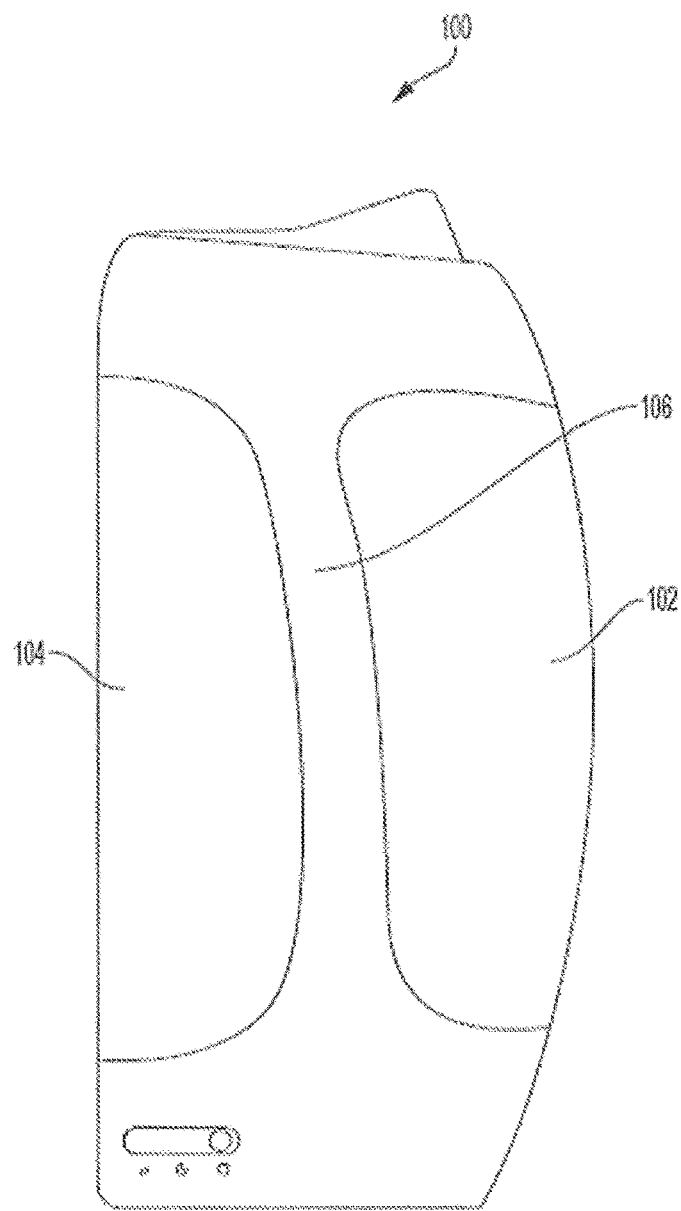
FIGS. 1A and 1B illustrate an exterior view of a vaporizer device according to an exemplary embodiment.

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Embodiments disclosed herein include an improved vaporizer device using a replaceable strip comprising either a plurality of dosage-controlled inhalable substance cartridges or a continuous band of inhalable substance disposed on a substrate comprising the replaceable strip. The cartridge sizes may contain enough inhalable substance for a single dose or multiple doses. The replaceable strip may attach to a movable conveyor belt system that rotates the replaceable strip along the conveyor belt and towards a heating unit, such as a heating coil, LED, or electric vaporizing unit, whereby the inhalable substance is vaporized to generate a gaseous version of the inhalable substance, such as tobacco vapor, cannabis vapor, atomized medicine, or other substances capable of being vaporized. The amount that the conveyor belt moves between inhalations may be based on the size of the cartridges or the size of the heating unit.

According to some embodiments, systems and methods can further comprise a flip-top mouthpiece connected to the vaporizer device. The flip-top mouthpiece may comprise a mouthpiece base, a mouthpiece portion, and a gasket. The mouthpiece base may snap into the vaporizer device, or the mouthpiece may connect to the vaporizer device by a hinge or similar types of apparatuses. The mouthpiece portion may form-fit into a hollow portion of the mouthpiece base. In addition, the gasket may create an airflow channel between the mouthpiece portion and the vaporizer device. The airflow channel created by the mouthpiece portion and the gasket may connect airflow tubing within the vaporizer device to a hollow tube within the mouthpiece portion thereby allowing air to flow from the airflow tubing within the vaporizer device out of the vaporizer device. This airflow channel allows a user to inhale a vaporized substance. The mouthpiece base may rotate such that no airflow occurs out of the vaporizer when the mouthpiece is positioned in a downward position but airflow may occur when the mouthpiece is positioned in an upward position. The gasket may engage the mouthpiece body when the mouthpiece is positioned in the downward position to create a seal that prevents air, odors, or vaporized substance from escaping from within the vaporizer device.

In yet another embodiment, the vaporizer device may increase a vaporizing temperature by a predetermined number of degrees, such as, for example, 1.5° C. or any temperature less than approximately 3° C., after every use or "pull" of the vaporizer device or according to some other predetermined method, such as after every rotation of the conveyor belt, every time the vaporizer device senses that airflow has ceased, or by a subsequent push of a button that activates a heating unit. As used herein, a "pull" of the vaporizer device may occur when a user inhales air through the vaporizer device to inhale the inhalable substance. A pull may also describe a dose or portion inhaled or when a vaporizer vaporizes the inhaled substance for a predetermined period of time.

FIG. 1A illustrates an exterior view of a vaporizer device 100 according to any exemplary embodiment. The vaporizer device 100 includes a plurality of removable doors 102, 104 connected to a middle structure 106, which may be in the form of an I-beam. The middle structure 106 may house the internal, non-removable components, such as a processor, a toggle switch, a heating unit, airflow tubes, and a temperature switch.

Figure 1B:
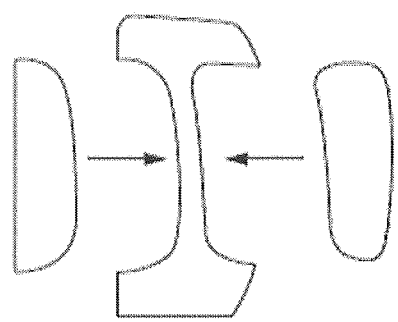

The doors 102, 104 may or may not be easily removed to replace certain components in the vaporizer 100. The doors 102, 104 may connect to the middle structure 106 through any mechanical method, such as snaps, prongs, or magnets. One of the doors 102 or 104 may open to reveal a conveyor belt (not shown). The conveyor belt may be stationary or removable. In a preferred embodiment, the conveyor belt is removable from the vaporizer device 100 so that a user can easily load strips onto the conveyor belt. Another door 102 or 104 may reveal or include a battery (not shown). The second door 102 or 104 may be omitted if the battery is rechargeable and not replaceable. The battery may be removable for recharging or replacement. The vaporizer device 100 may further comprise a wire port (not shown), such as, for example, a USB port or a similar type of port, to receive power and recharge the battery. In some embodiments, the battery is not rechargeable, and the wire port may be omitted if the battery is not rechargeable. According to an exemplary embodiment, the wire or USB port may also connect to a computer to configure the processor of the vaporizer device 100. In yet another embodiment, the battery is omitted, and the vaporizer device receives power from a wall outlet. In some embodiments, the battery is a super capacitor or an organic super capacitor. The second door 102 or 104 may reveal other internal components, such as the airflow tubes, which may be removed for cleaning. FIG. 1B illustrates the doors 102, 104 being separated from the middle structure 106.

Figure 2A:
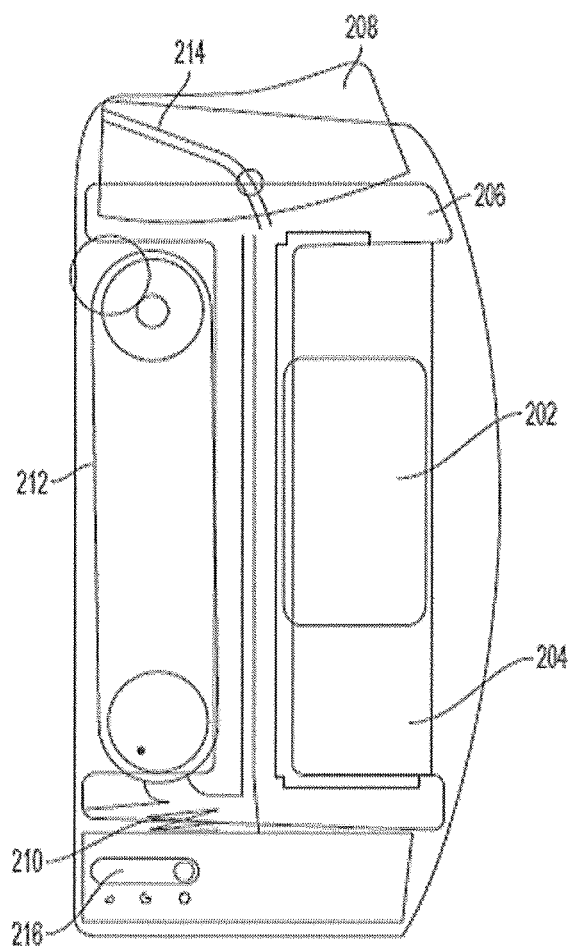
FIGS. 2A, 2B, and 2C illustrate a projection view of the vaporizer device according to an exemplary embodiment.

FIG. 2A illustrates a projection view of the vaporizer device 100 to illustrate the internal components of the vaporizer device 100. The internal components may comprise a processor 202, a battery 204, an interior frame 206, a toggle switch 208, a heating unit 210, a conveyor belt 212, airflow tubing 214, and a temperature switch 216.

The processor 202 may control the heating temperature at which the heating unit 100 vaporizes an inhalable substance. The processor 202 may further control the movements of the conveyor belt 212. For example, the processor 202 may lock the conveyor belt 212 in place until the heating unit 210 has vaporized the inhalable substance.

The processor 202 may control the conveyor belt 212 according to one of a plurality of different methods. For example, the processor 202 may be programmed to detect how many doses or "pulls" are associated with a cartridge of an inhalable substance strip. For example, each cartridge may comprise a single pull or dose, or each cartridge may comprise multiple doses or pulls. The number of pulls or doses per cartridge may be set by the manufacturer of the cartridge strip, by the manufacturer of the vaporizer device, or set by the user as a configuration parameter. The processor 202 may index and keep track of the number of pulls that have occurred per cartridge. The indexed number may reset each time the conveyor belt 212 moves to place a new cartridge adjacent to the heating unit or whenever the processor 202 detects that cartridge has been used up.

Figure 11:
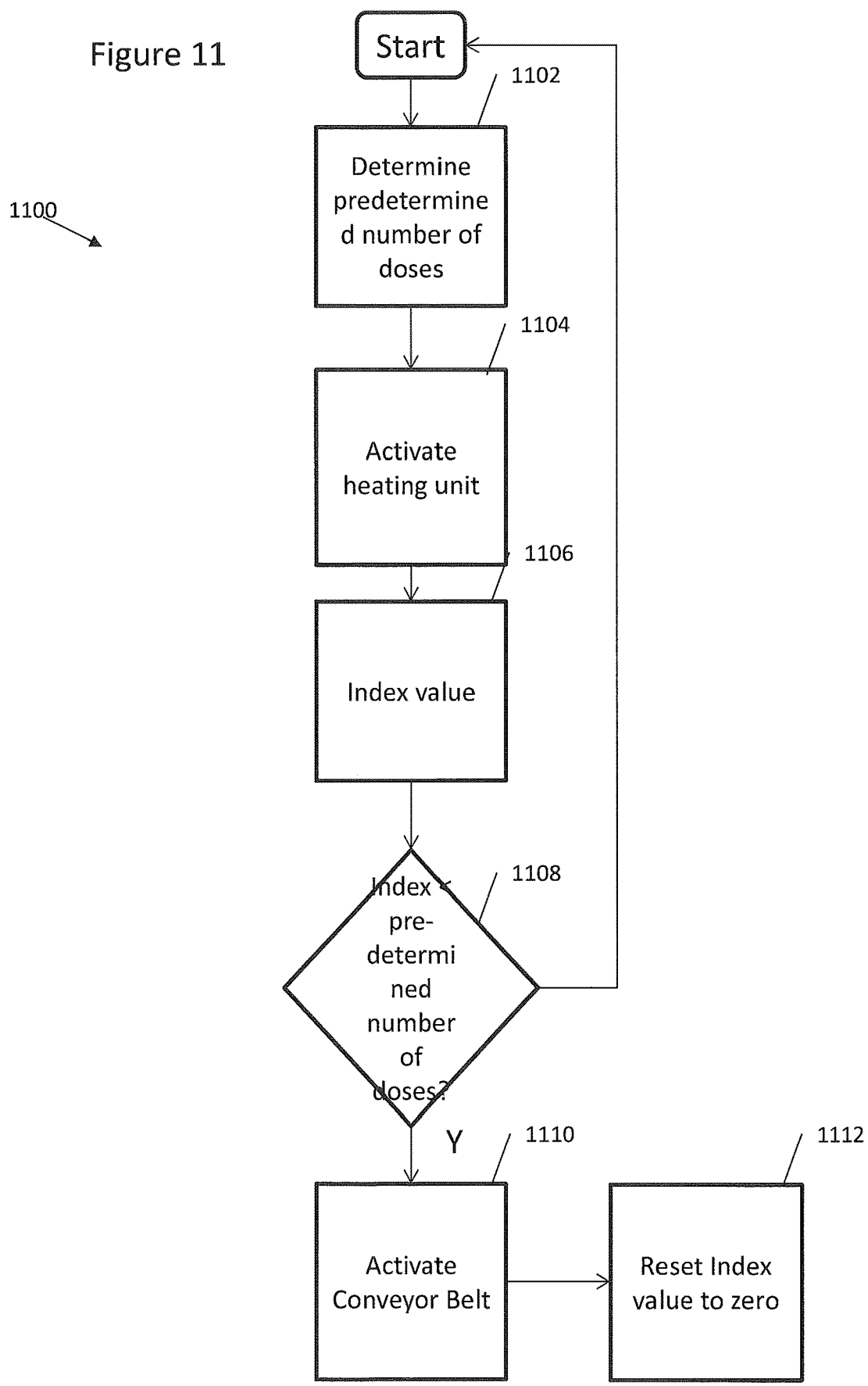
FIG. 11 illustrates a method for indexing a value to track a number of doses according to an exemplary embodiment.

FIG. 11 illustrates an exemplary method 1100 for tracking the number of doses or pulls remaining for a cartridge or portion of the continuous band. In step 1102, the processor 202 determines a number of pulls or doses associated with each cartridge or portion of the continuous band. In step 1104, the processor 202 activates the heating unit 210 to vaporize the inhalable substance. In step 1106, the processor 202 indexes a value that counts the number of doses or pulls performed by the user for a specific cartridge or portion of the continuous band. In step 1008, the processor 202 determines whether the indexed value is equal to the predetermined number of pulls or doses. If the indexed value is less than the predetermined number, the processor 202 moves back to step 1104 to activate the heating unit 210 to again vaporize the cartridge or portion of the continuous band. If the processor 202 determines that the indexed value is not less than the predetermined value, the processor 202 activates the conveyor belt 212 in step 1110 and resets the indexed value to zero in step 1112.

For example, if each cartridge contains two doses (e.g. approximately a cartridge that is 2 mm thick in size), the processor 202 would determine if the user has inhaled twice and restrict movement of the conveyor belt 212 until the processor 202 has counted two pulls. Once the processor 202 detects that the conveyer belt 212 has positioned a new cartridge adjacent to the heating unit 210, the index value would be reset to 0. In another embodiment, the vaporizer device 100 may include sensors to determine if any inhalable substance remains in a cartridge or at a point in a continuous strip. The sensor may determine the existence of inhalable substance in a cartridge according to any known sensor configuration, such as e.g. an optical sensor, heat sensor, or infrared sensor. In yet another embodiment, the replaceable strip is not divided into cartridges but comprises a continuous band of the inhalable substance (FIG. 3B). In the continuous band embodiment, the processor 202 may operate in a manner similar to the cartridge embodiment but the movement of the conveyor belt 212 may differ slightly as the entire length of the replaceable strip comprises the inhalable substance. In this continuous band embodiment, the conveyor belt 212 may move in smaller increments. The continuous band embodiment may also index inhales by the user.

The processor 202 may further control the activation of the heating unit 210. The processor 202 may detect when a user wants to activate the heating unit 100 by determining if a physical button or switch has been activated by a user. In another embodiment, the vaporizer device 100 may comprise an airflow sensor to determine if air is flowing at a predetermined rate through the airflow tubing 214, which would indicate that a user is attempting to inhale or pull air through the vaporizer device 100. When the airflow sensor detects airflow, the airflow sensor can send a signal to the processor 202 indicating that the user is attempting to inhale the inhalable substance. In response to this signal, the processor 202 may activate the heating unit 210 to begin vaporizing the inhalable substance. Thus, in this embodiment, the vaporizer device 100 can automatically activate the heating unit 210 in response to the user pulling air through the vaporizer device 100. The processor 202 may activate the heating unit 210 for a predetermined period of time (e.g. 3 seconds) or as long as the airflow sensor is detecting airflow.

Although not illustrated in FIG. 2A, the vaporizer device 100 may further comprise a display unit. The display unit may display a plurality of information to the user about the vaporizer device 100, such as, for example, a vaporizing temperature, remaining full cartridges, number of pulls remaining on a cartridge, percentage of material remaining in the cartridge, and battery power level.

Figure 2B:
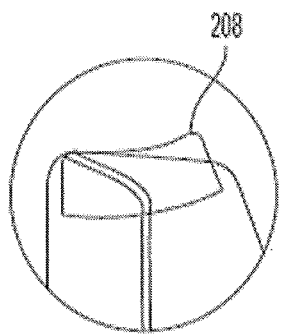
Figure 2C:
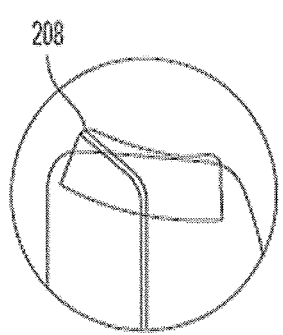

The vaporizer device 100 also includes a toggle mouthpiece 208 that may toggle to restrict or engage airflow. The toggle mouthpiece may further comprise the mouthpiece design described below with reference to FIGS. 6-8. As shown in FIG. 2B, the toggling mouthpiece 208 may rotate between a first position and a second position. When in the first position (i.e. the closed position) (FIG. 2B), the toggle mouthpiece 208 may block airflow through the airflow tubing 214 because the airflow tubing 214 is blocked by the housing of the vaporizer device 100. When in the second position (i.e. the open position) (FIG. 2C), the user may inhale air through the airflow tubing 214 because the airflow tubing 214 is exposed.

FIG. 2A illustrates the temperature switch 216 as having three settings, but the vaporizer device 100 may comprise more or fewer temperature settings.

The temperature switch 216 (or dial, or digital setting) allows a user to quickly switch between temperature settings at which the heating unit 210 vaporizes the inhalable substance. For example, in a first setting, the heating unit 210 may sublimate or extract or vaporize the inhalable substance at a temperature higher than a second setting. The temperature at which the heating unit 210 vaporizes the inhalable substance may be configured and adjusted by a user through an external software application, such as a mobile application executed by a mobile device, such as a smart phone. The external software application may allow a user to select a specific vaporizing temperature for each setting. For example, in the exemplary three setting embodiment, a user may set the first setting to cause the heating unit 210 to sublimate or extract or vaporize at 380° F., set the second setting to cause the heating unit 210 to sublimate or extract or vaporize at 340° F., and set the third setting to cause the heating unit 210 to vaporize or extract or sublimate at 280° F. From here on, the exemplary embodiments will only describe the vaporizer device 100 as vaporizing an inhalable substance, but it is assumed that the vaporizer device 100 can sublimate, extract, or perform any other action on the inhalable substance to transform the inhalable substance into a gaseous form. The different temperature settings may also correspond to different vaporizing temperatures for different inhalable substances (e.g. the first temperature setting is for tobacco, the second temperature setting is for hookah, and the third temperature setting is for cannabis).

Figure 12:
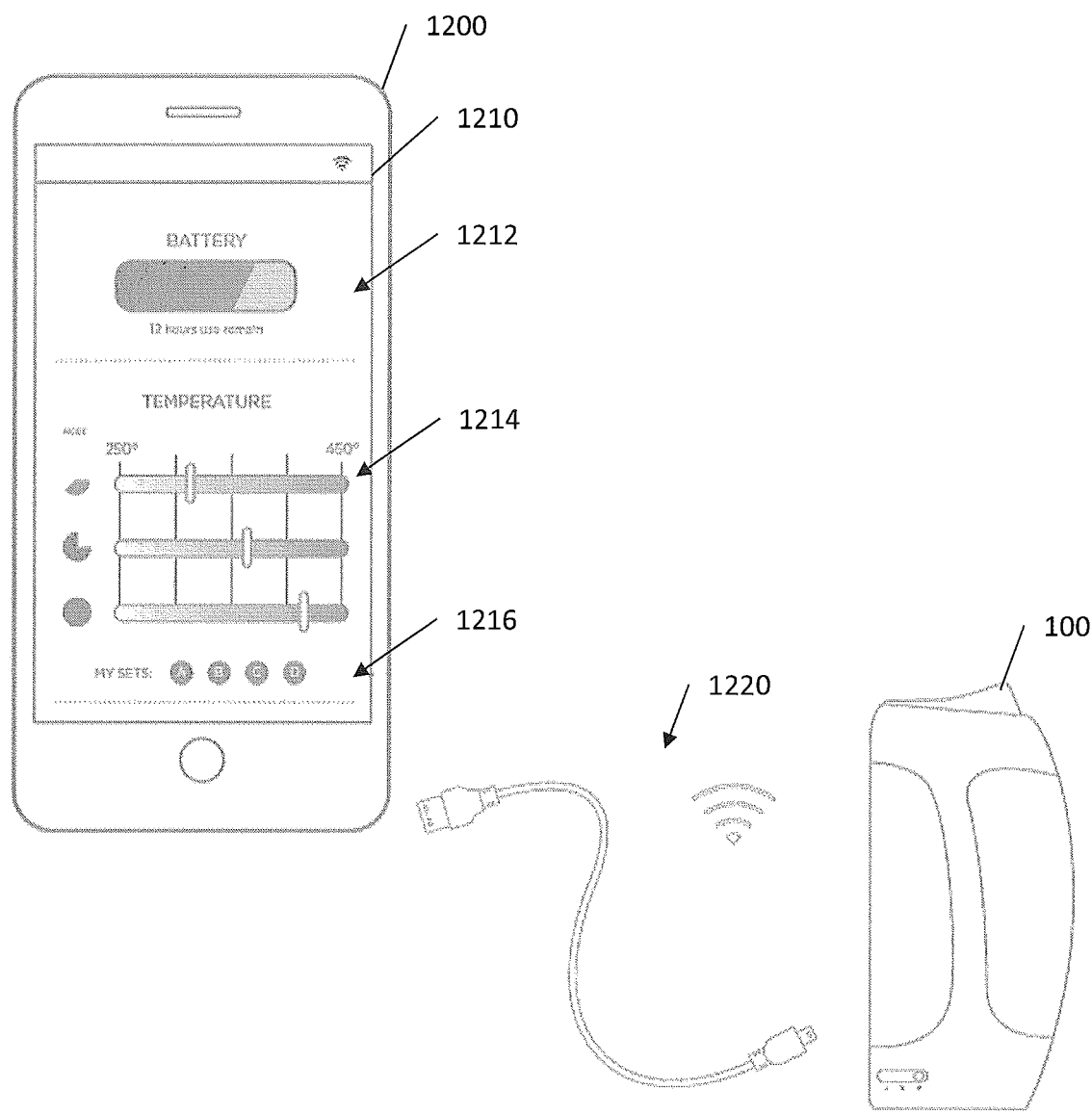
FIG. 12 illustrates a graphical user interface displaying information about the vaporizer device according to an exemplary embodiment.

FIG. 12 illustrates a first graphical user interface (GUI) 1210 of the external software application presented on the mobile device 1200. As shown in FIG. 12, the mobile device 1202 can connect to the vaporizer device 100 via a wired (e.g. USB) or wireless (e.g. WiFi or Bluetooth) connection 1220. When the mobile device 1200 connects to the vaporizer device 100, the mobile device 1200 can display information about the vaporizer device 100 using the external software application via GUIs, such as the first GUI 1210. While the external software application is illustrated on the mobile device 1200, the external software application can also be executed on a PC or any other electronic equipment.

As illustrated in FIG. 12 according to an exemplary embodiment, the first GUI 1210 may include a battery display portion 1212, a settings portion 1214, and a presets portion 1216.

The battery display portion 1212 displays a battery percentage for the vaporizer device 100. The battery display portion 1212 may illustrate the battery percentage using different colors depending on the battery percentage. The battery display portion 1212 may also illustrate a time remaining for a current battery charge (e.g. FIG. 12 illustrates that the battery has 12 hours remaining).

The settings portion 1214 may include three adjustable configuration bars for each mode. The configuration bars may correspond to a vaporizing temperature. For example, a user may slide a slider along the configuration bars to change a vaporization temperature for three different modes. The slider may slide to any temperature between 250° C. and 450° C.

Finally the presets portion 1216 may include one or more (e.g. FIG. 12 illustrates four presets) presets for the temperature configurations (e.g. FIG. 12 illustrates four presets). By merely interacting with one of the preset buttons, the external software application may automatically move the sliders on the configuration bars in the settings portion 1214 to preset temperatures.

Figure 13:
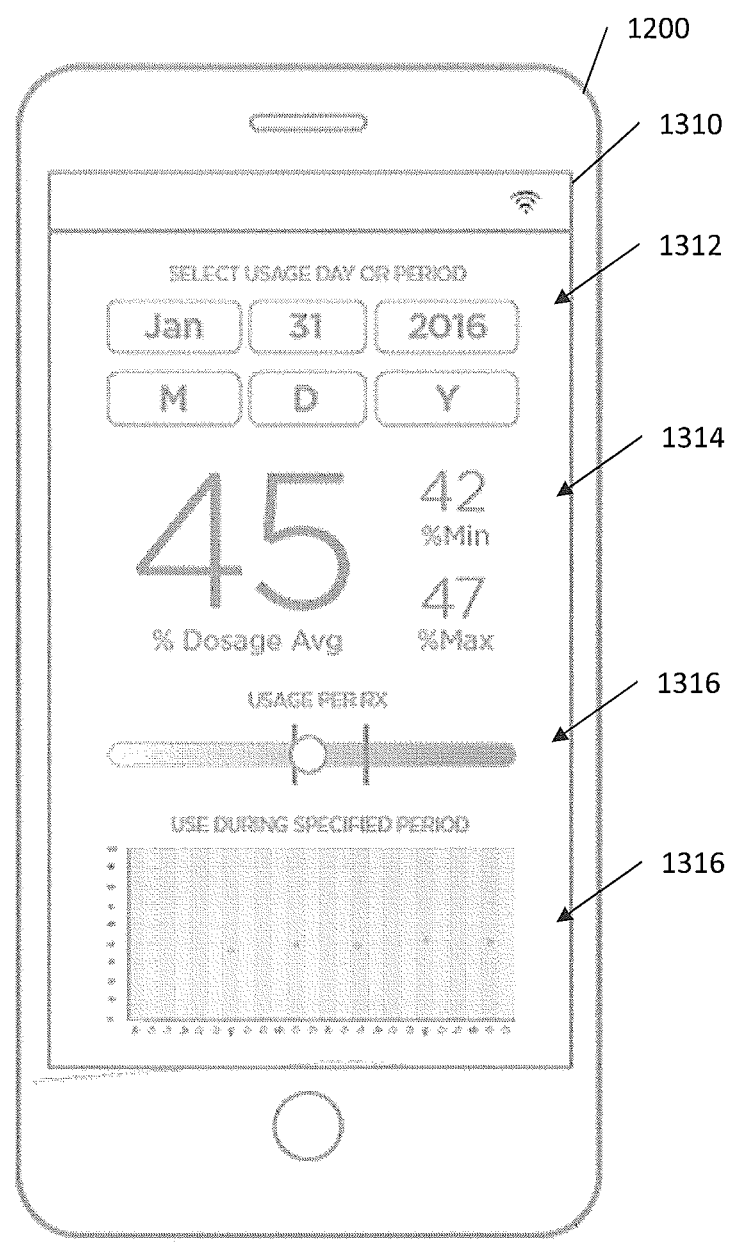
FIG. 13 illustrates a graphical user interface displaying information about use of the vaporizer device according to an exemplary embodiment.

FIG. 13 illustrates a second GUI 1310 of the external software application presented on the mobile device 1200. The second GUI 1310 may include a date portion 1312, a usage statistics portion 1314, a usage thresholds slider 1316, and a usage graph 1318. These statistics may be used by a medical professional to accurately track history and use of the vaporizer device 100 by a patient.

The data portion 1312 allows a user or medical professional to select a date or timeframe to analyze use of the vaporizer device 100. The user or medical professional can select a single date or multiple dates to select a timeframe. The date portion 1312 may also include minutes and hours selection for a more granular analysis.

The usage statistics portion 1314 may display a dosage average percentage. The usage statistics portion 1314 may also display minimum and maximum usage percentages as set by the usage threshold slider 1316. The minimum and maximum usage percentages may corresponding to a medical professional's prescription.

The usage threshold slider 1316 may display the minimum and maximum usage percentages as vertical bars and also the average usage percentage as a slider on the bar.

Finally, the usage graph 1318 displays usage over a timeframe. For example, the usage graph 1318 may plot the average usage percentage over a timeframe (e.g. 30 days).

The mobile application may upload these configurations to the vaporizer device 100 through a wired or wireless connection. In a wired embodiment, the vaporizer device 100 may include a wire port, such as a USB port, to receive instructions from the mobile application. Alternatively or additionally, the vaporizer device 100 may include a wireless transceiver, such as a Bluetooth transceiver, Zigsbee transceiver, WiFi transceiver, NFC transceiver, or any other wireless transceiver, and the vaporizer device 100 may receive temperature settings wirelessly over a paired Bluetooth connection or any other wireless connection. In yet another embodiment, a user may select temperature parameters on a website, and the vaporizer device 100 may receive the temperature parameters from a server over the Internet using a wireless network transceiver, such as a WiFi chip. The mobile application may also connect to a cloud that saves preferences, data related to use of the vaporizer device 100, or any other data. Users and doctors may access this cloud via different credentials.

In some embodiments, the vaporizer device 100 may come pre-configured and the vaporizing temperature associated with each mode may not be configurable by a user.

Upon receiving the temperature settings according to any known communication method, the processor 202 stores the temperature settings on computer readable medium. The processor 202 may determine which mode to vaporize the inhalable substance by determining a position of the temperature switch 216. The physical switch 216 may be omitted and replaced with digital settings that are reported on a display. Based on the temperature switch's 216 position or digital settings, the processor 202 instructs the heating unit 210 to heat at the temperature selected by the user.

The heating unit 210 may be any convection heater, such as a heating coil. In another exemplary embodiment, the heating unit 210 may be a laser emitting diode or a light emitting diode ("LED"). The temperature generated by the heating unit 210 may increase by sending more current through the heating unit 210. The amount of current flowing through the heating unit 210 may be controlled by the processor 202. The amount of current necessary to heat the heating unit 210 to each selectable temperature may be saved in a look-up table in computer-readable memory, and the processor 202 may reference the look-up table before commanding the heating unit 210.

When activated, the heating unit 210 generates heat adjacent to a cartridge or strip having the inhalable substance. The heat generated by the heating unit 210 vaporizes the inhalable substance. A user inhales air through the vaporizer device 100, thereby moving air past the vaporized inhalable substance and through the airflow tubing 214 to the toggle mouthpiece 208 where the user is inhaling. The inhaled air with the vaporized inhalable substance is thereby delivered to the user.

The conveyor belt 212 may be controlled by a manual switch or by the processor 202. In either embodiment, the conveyor belt 212 movement may be controlled by a conveyor belt control. The conveyor belt control may restrict movement of the conveyor belt 212 to only one direction. Furthermore, the conveyor belt control may restrict the amount of movement so that a cartridge or unvaporized portion of the continuous band is always properly placed adjacent to the heating unit 210 for optimal vaporization. If the conveyor belt 212 is moved manually, the convertor belt control may indicate proper placement of a cartridge with a click or by restricting movement past a position adjacent to the heating unit 210. The conveyor belt control may allow movement of the conveyor belt 212 only after a cartridge has been exhausted.

Figure 3A:
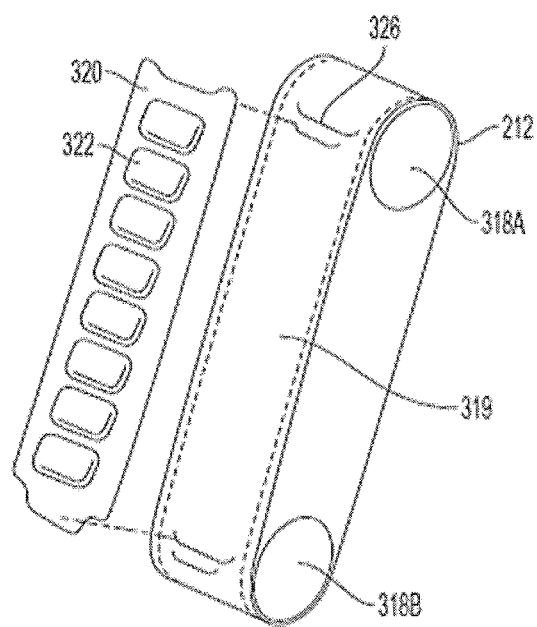
FIGS. 3A and 3B illustrate a conveyor belt and a replaceable strip for use in the vaporizer device according to an exemplary embodiment.
Figure 3B:
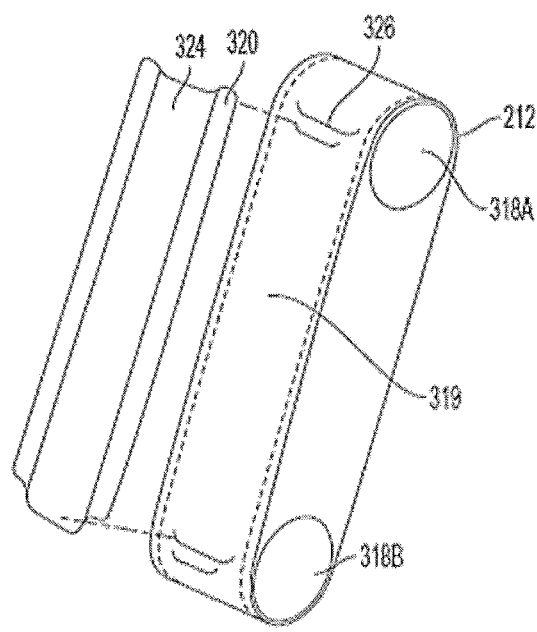

Referring to FIGS. 3A and 3B, the conveyor belt 212 is illustrated. As shown in FIG. 3A, a replaceable strip 320 may comprise a plurality of cartridges 322, and each cartridge comprises inhalable substance. As shown in FIG. 3B, the replaceable strip 320 may comprise a continuous band 324 of inhalable substance. The replaceable strip 320 may comprise a substrate on which either the cartridges 322 or the continuous band 324 are disposed.

The processor 202 may control an electric motor connected to gears 318A, 318B controlling movement of the conveyor belt 212 to move the conveyor belt automatically. In either embodiment, an LED may provide feedback indicating whether a cartridge 322 is in place adjacent to the heating unit 210. The LED may also provide feedback indicating whether an unvaporized portion of the continuous band 324 is in place adjacent to the heating unit 210. For example, the LED may be red or off when the cartridge 322 or unvaporized portion is not positioned adjacent to the heating unit 210, and the LED may be blue or green when the cartridge 322 or unvaporized portion is positioned adjacent to the heating unit 210. The processor 202 may control the conveyor belt 212 based on the reading of sensors or using the indexing technique described above. The processor 202 may command the electric motor to move the conveyor belt 212 to position the replaceable strip 320 such that an unused cartridge 322 is adjacent to the heating unit 210 in response to user input, such as pressing a button, or automatically after detection of an exhausted cartridge 322. The amount the conveyor belt 312 moves may be uniform based on a uniform cartridge and cartridge strip size or based on the size of the heating unit 210.

The conveyor belt 212 may include two toothed cogs 318A, 318B and a belt 319 forming the conveyor belt 212. The belt 319 may wrap around the toothed cogs 318A, 318B and rotate around the cogs 318A, 318B according to the movement of the cogs 318A, 318B. The cogs 318A, 318B may be restricted from moving by the conveyor belt control, and the cogs 318A, 318B may move in response to the manual switch or an electric motor connected to at least one of the cogs 318A, 318B.

The belt 319 may include connectors 326 that hold the replaceable strip 320 on the belt 319. The connectors 326 may comprise any mechanical connection means such as slits that receive ends of the replaceable strip, clips, protrusions that snap into holes on the replaceable strip 320, Velcro, or any other connection means for temporarily fixing the replaceable strip 320 to the belt 319. When connected, the replaceable strip 320 moves with the movement of the belt 319.

Figures 4A, 4B:
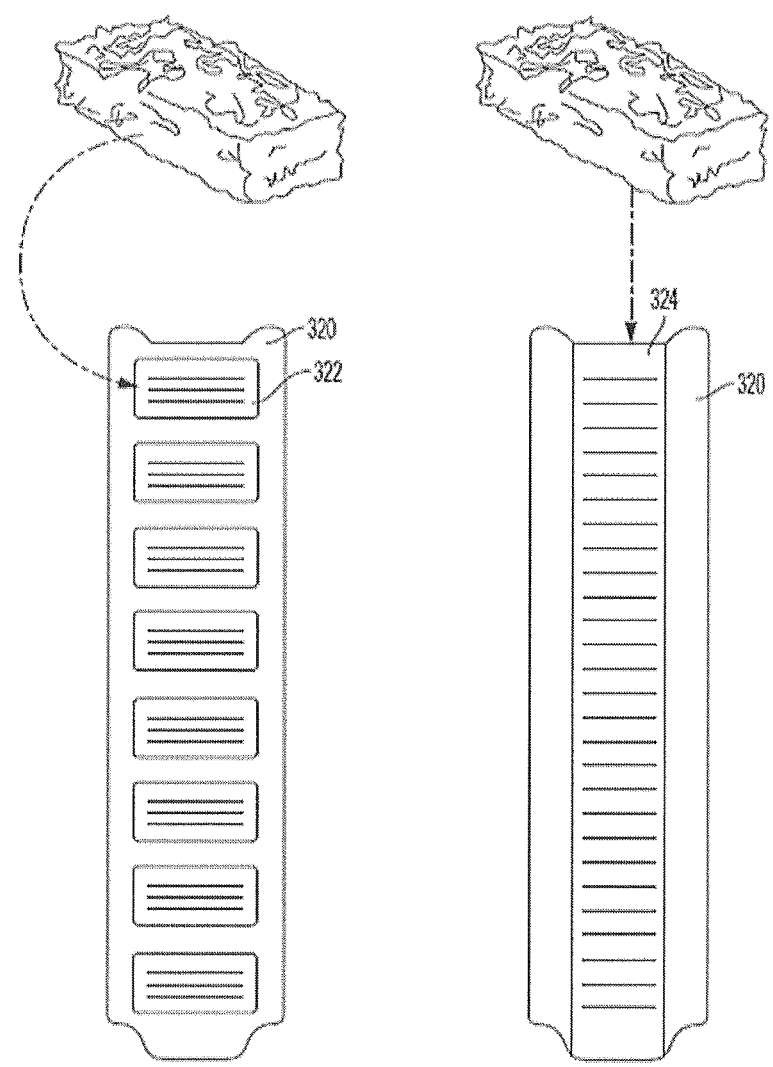
FIGS. 4A and 4B illustrate cartridges in the replaceable strip according to an exemplary embodiment.

Referring now to FIG. 4A, multiple replaceable strips 320 may also connect to each other around the belt 319. The replaceable strip 320 may be flexible to wrap around the cogs 318A, 318B of the conveyor belt 312 and follow the belt 319. In the cartridge embodiment, the cartridges 322 may also be flexible to wrap with the replaceable strip 320. In the continuous band 326 embodiment (FIG. 4B), the continuous band 326 may also be flexible to wrap with the replaceable strip 320.

According to an exemplary embodiment, the replaceable strip 320 may include any number of cartridges 322, although FIG. 4A illustrates eight cartridges. Each cartridge 322 may hold a vacuum-packed serving of the inhalable substance, such as tobacco. Before inserting the replaceable strip 320 into the vaporizer device 100, a user may peel a vacuum-packed plastic off the replaceable strip 320. The inhalable substance may be held in place within the replaceable strip 320 by one or more prongs or tabs. The tabs or prongs may engage the inhalable substance in a solid form to hold the inhalable substance in the replaceable strip 320 as the replaceable strip 320 moves with the movements of the conveyor belt 212. The cartridges 322 may hold the inhalable substance in ground form, leaf form, or gel form, but the cartridges 322 is not limited to only these forms.

The user can replace a used replaceable strip 320 by opening the door 102, 104 and replacing a used replaceable strip 320 with a full replaceable strip 320. The user can also replace multiple replaceable strips 320 by removing the conveyor belt 212 and replacing multiple used replaceable strips 320. The processor 202 can provide indication when the replaceable strip 320 is ready to be replaced via an illuminated LED or an LCD display.

FIG. 5 illustrates a method 500 for controlling the conveyor control system. The method 500 begins with step 502 with the processor 202 determining if the conveyor belt door 102, 104 is closed. If the door 102, 104 is open, the processor 202 restricts current to flow through the heating unit 210 and restricts movement of the conveyor belt 212 in step 504. If the door 102, 104 is closed, the processor 202 allows the conveyor belt motor (or manual switch) to move the conveyor belt 212 to position a cartridge 322 or unvaporized portion of the continuous band 324 adjacent to the heating unit 210 in step 506. The distance to move the conveyor belt 312 may be fixed and predetermined based on a size of the cartridges 322 or the heating unit 210. In step 508, the processor 202 determines whether the cartridge 322 or unvaporized portion of the continuous band 324 is in place adjacent to the heating unit 210. If the cartridge or unvaporized portion of the continuous band 324 is not adjacent to the heating unit 210, the processor 202 returns to step 506 and allows movement of the conveyor belt 212. Once the conveyor belt 212 moves the predetermined distance, the processor 202 commands the conveyor belt control to restrict movement of the conveyor belt 212 in step 510. In step 512, the processor 202 then determines whether a user desires to inhale the inhalable substance, such as by detecting airflow or detecting the activation of a button. When airflow is detected, the processor engages the heating unit 210 to vaporize the inhalable substance in step 514. A number of pulls or doses per cartridge 322 or portion of the continuous band 324 may also be predetermined in step 516. The processor 202 counts a number of times the user has pulled or inhaled from a single cartridge or portion of the continuous band 324. The processor 202 determines if the user has inhaled or pulled the predetermined number of times per cartridge 322 or portion of the continuous band 324, and if the user has inhaled the predetermined number of times, the processor 202 engages the conveyor belt control to allow movement of the conveyor belt 212 in step 518. If the user has not inhaled the predetermined number of times, the processor 202 returns to step 512 and again determines whether the user is inhaling. This step may include the processor 202 commanding the motor to move the conveyor belt 212 the predetermined distance.

The processor 202 may interact with computer-readable memory to save data regarding how the vaporizer device 100 has functioned to determine user preferences and also to help in medical charting or diagnosis. The processor 202 may save in the memory the number of times the vaporizer device 100 has been used, the number of cartridges 322 vaporized, the number of doses vaporized, the types of inhalable substances vaporized, the heating conditions and temperatures used to vaporize the inhalable substances, or any other data that might be relevant and tracked by the processor 202. The information saved to the memory may be uploaded to another computer or a server, such as a medical computer terminal used by doctors to track patient data. A doctor may reference, for example, the number of doses inhaled by a patient over time, and consult with the patient to see if a medical condition has improved. For example, the doctor may determine whether pain has decreased as a result of a certain dosage of a prescribed inhalable substance. The doctor may use this information to chart additional patient data, make a determination whether to increase or decrease the dosage, or prescribe a different inhalable substance. A user may also download this information to a personal device, for example through the mobile application, to view statistics on the substances vaporized by the vaporizer device. For example, the user can determine what types of inhalable substances are most frequently vaporized, the average temperature used for vaporization, most popular vaporization temperature, the number of doses or cartridges 322 inhaled over the life of the vaporizer device 100, or any other data.

Figures 6A, 6B:
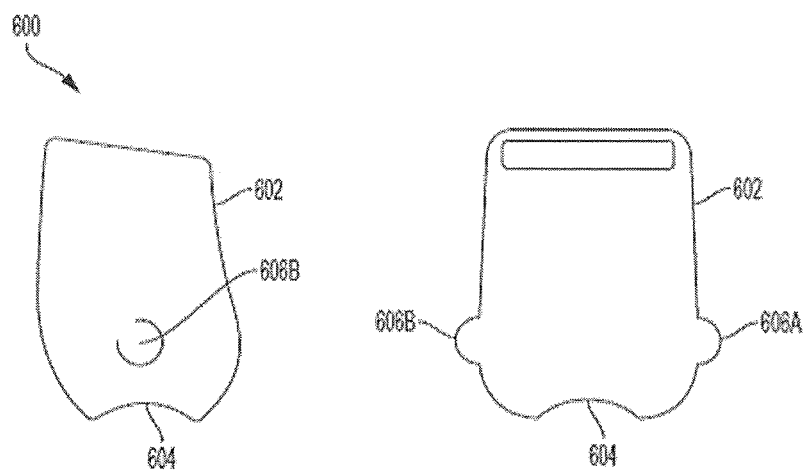
FIGS. 6A and 6B illustrate a molded mouthpiece base according to an exemplary embodiment.
Figure 7A:
FIGS. 7A and 7B illustrate a mouthpiece portion according to an exemplary embodiment.
Figure 7B:
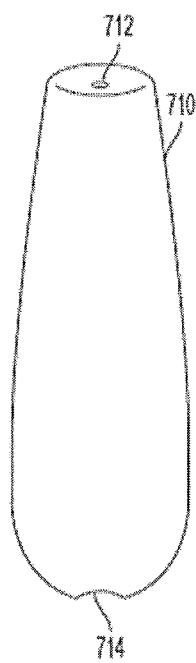

FIGS. 6-8 illustrate a mouthpiece 600 for the vaporization unit 100. FIGS. 6A and 6B illustrates a mouthpiece base 602. The mouthpiece base 602 may be molded from quality, healthy, or medical grade materials. The mouthpiece base 602 may be hollow to receive a mouthpiece portion 710 (FIG. 7B). The mouthpiece base 602 also includes a hole 604 where a gasket may protrude through the mouthpiece base 602 to engage the mouthpiece portion 710. Furthermore, the mouthpiece base 602 may include tabs 606A, 606B that engage the vaporizer device. The tabs 606A, 606B are notches that fit within indents in the vaporizer device 100. The mouthpiece base 602 may rotate substantially 90° about the tabs 606A, 606B. In other embodiments, the tabs 606A, 606B are replaced by a hinge. In either embodiment, the mouthpiece 600 rotates to close airflow through the mouthpiece 600 and prevent odors from escaping the vaporizer device 100.

FIGS. 7A and 7B illustrate the mouthpiece portion 710 that is inserted into the mouthpiece base 602. The mouthpiece portion 710 may be tapered to form-fit into the mouthpiece base. The mouthpiece portion 710 may comprise a bulbous bottom portion to engage with the gasket. The mouthpiece portion 710 may comprise stainless steel, plastic, rubber, ceramic, glass, or any other well-known substance. The mouthpiece portion may include a tube 712 that forms a hollow portion from a top portion of the mouthpiece portion 710 to a hole 714 in the bottom of the mouthpiece portion 710. Vapor from the vaporizer device 100 may be inhaled by the user through the tube 712.

FIG. 8A illustrates the mouthpiece portion 710 engaging and fitting within the mouthpiece base 602. The mouthpiece 600 includes a tube 712 that extends the length of the mouthpiece 600.

FIG. 8B illustrates the mouthpiece portion 710 inserted into the mouthpiece base 602 and engaging the gasket 820. The gasket 820 seals the mouthpiece 600 to the airflow tubing 214 of the vaporizer device 100. Vaporized substance may flow through the airflow tubing 214, through the gasket 820, and through the tube 712 of the mouthpiece to allow a user to inhale the inhalable substance when the mouthpiece base 602 and the mouthpiece portion 710 are positioned in the upright position.

As shown in FIG. 8C, the entire mouthpiece 600 may rotate together to restrict or engage airflow through the mouthpiece 600. When in the downward position, air, vapor, inhalable material, or odors do not leave the vaporizer device 100. When in the upward position, a user may inhale air and the inhalable substance from the vaporizer device 100. In another embodiment, a hole 604 at the bottom of the mouthpiece portion 602 swings to match with the airflow tubing 214. When in the downward position, the airflow tubing 214 may be blocked by the gasket 820 and the mouthpiece base 602 to prevent air and odors from escaping the vaporizer device 100. As additional protection, the mouthpiece portion 710 may engage a housing 830 of the vaporizer device to also prevent air and odors from escaping the vaporizer device 100.

Figure 9B:
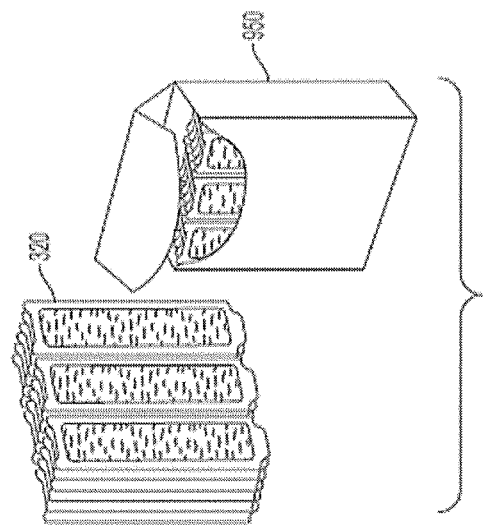
FIGS. 9A and 9B illustrate a replaceable strip having a continuous band of inhalable substance according to an exemplary embodiment.
Figure 9A:
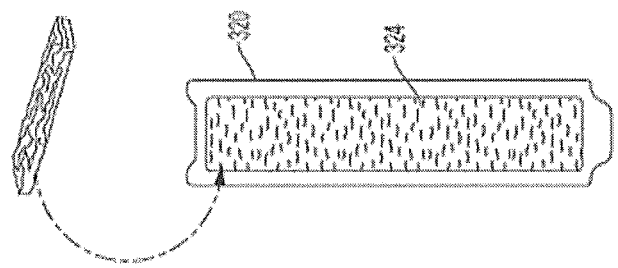

FIG. 9A again illustrates a replaceable strip 320 including a continuous band 324. In the embodiment shown in FIG. 9A, the continuous band 324 may not extend the entire length of the replaceable strip. The continuous band 324 comprises inhalable substance, and the continuous band 324 of the inhalable substance is disposed on a substrate comprising the replaceable strip 320. FIG. 9B illustrates that a plurality of replaceable strips 320 may be contained within a container 950 and sold in packs.

The vaporizer device 100 also includes an incremental temperature raising program. The incremental temperature raising program may vaporize an inhalable substance at a first temperature for during a first inhale or "hit", which may vaporize the inhalable substance at a pre-set temperature. If some of the inhalable substance remains in the vaporizer device, the processor 202 raises the vaporizing temperature by a predetermined amount, such as e.g. 1.5-2° C. Raising the vaporizing temperature by a relatively small amount on an inhalable substance that has been previously vaporized completely extracts the flavor or desired ingredient in subsequent hits. So, during a second hit, the heating unit 210 heats the remaining inhalable substance at the raised temperature value. For example, the first vaporizing temperature may be 330° F., and the second vaporizing temperature may be 332.7° F.

The predetermined temperature increase may be configured by a user, for example using the mobile application described above. The user may also configure the number of times the temperature increases (such as only after the first and second hits, or indefinitely).

The incremental temperature increase program may occur in the cartridge embodiment described above or in vaporizer devices that receive inhalable substances according to other methods. The incremental temperature increase program may apply to any vaporizer.

Figure 10:
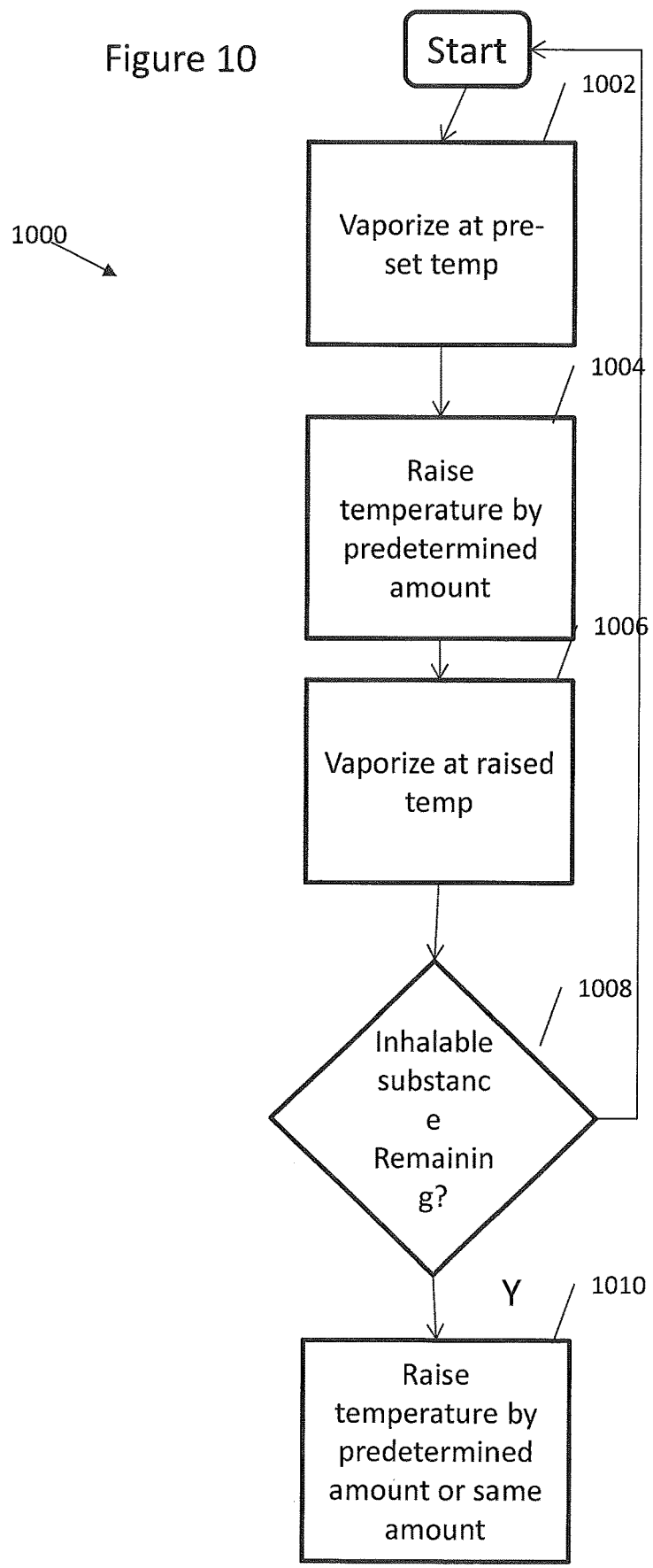
FIG. 10 illustrates a method for incrementally increasing a vaporization temperature according to an exemplary embodiment.

FIG. 10 illustrates a method 1000 for an incremental temperature increase program. The method 1000 begins by vaporizing the inhalable substance at a predetermined temperature at step 1002. The predetermined temperature may be set by a user through the mobile application. The processor 202 may determine the predetermined temperature and generate an activate first temperature command that commands the heating unit to vaporize the inhalable substance at the predetermined temperature.

Next, the processor 202 raises the vaporizing temperature by a predetermined amount (such as e.g. 1.5-2° C.) in step 1004, and vaporizes the inhalable substance at the raised temperature in step 1006. The processor 202 may determine the raised temperature and generate an activate second temperature command that commands the heating unit to vaporize the inhalable substance at the raised temperature.

After vaporizing the inhalable substance at the raised temperature, the processor 202 determines if any inhalable substance remains in step 1008, such as by the indexing process described above or using any sensors. If no inhalable substance remains, the process restarts at step 1002 when more inhalable substance is ready to be vaporized or the conveyor belt 212 moves to position an unused cartridge 322 adjacent to the heating unit 210. If some inhalable substance remains, the processor 202 determines if it should raise the temperature by the predetermined amount again or remain at the same temperature in step 2014. This determination may depend on preferences of the user. The processor 202 will vaporize the remaining inhalable substance at the raised temperature of the same temperature depending on the user preferences or a preset temperature, which may be saved in memory. The user may determine the raised temperature amount in increments of e.g. 0.1° C.

Although a few embodiments have been described in detail above, other modifications are possible. For example, the logic flows described above do not require the particular order described, or sequential order, to achieve desirable results. Other steps may be provided, or steps may be eliminated, from the described flows, and other components may be added to, or removed from, the described systems. Other embodiments may be within the scope of the invention.

From the foregoing, it will be observed that numerous variations and modifications may be effected without departing from the spirit and scope of the invention. It is to be understood that no limitation with respect to the specific system or method described herein is intended or should be inferred. It is, of course, intended to cover all such modifications as fall within the sprit and scope of the invention.

What is claimed is:

1. A vaporizer device comprising:
    airflow tubing configured to deliver a gaseous substance to a user;
    a mouthpiece base configured to rotate between a first position and a second position;
    a gasket coupled between the mouthpiece base and the airflow tubing; and
    a mouthpiece portion configured to couple to the mouthpiece base,
    wherein the mouthpiece base prevents the gaseous substance from escaping the airflow tubing in the first position and the mouthpiece base allows the gaseous substance to escape the airflow tubing in the second position, and
    wherein the mouthpiece base engages the gasket in the first position to prevent the gaseous substance from escaping the airflow tubing.

2. The vaporizer device of claim 1 wherein the mouthpiece base rotates substantially 90° from the first position to the second position.

3. The vaporizer device of claim 1 further comprising a housing.

4. The vaporizer device of claim 3 wherein the mouthpiece portion engages the housing in the first position, and wherein the mouthpiece base and mouthpiece portion are positioned upward from the housing in the second position.

5. The vaporizer device of claim 3 wherein the mouthpiece base is coupled to the housing.

6. The vaporizer device of claim 5 wherein the mouthpiece base is coupled to the housing through tabs that fit within indents in the housing.

7. The vaporizer device of claim 5 wherein the mouthpiece base is coupled to the housing via a hinge.

8. The vaporizer device of claim 1, wherein the mouthpiece base includes a hole, and wherein the gasket protrudes through the hole when the mouthpiece base is in the second position.

9. The vaporizer device of claim 8, wherein the mouthpiece portion includes a tube extending through the mouthpiece portion, and wherein the tube engages the gasket to allow the gaseous substance to flow through the airflow tubing, the gasket, and the tube to deliver the gaseous substance to the user.

10. The vaporizer device of claim 1 wherein the mouthpiece base comprises a bulbous bottom portion.

11. The vaporizer device of claim 10 wherein the mouthpiece portion is tapered to form-fit into the mouth piece base.

12. A vaporizer device comprising:
    a housing;
    airflow tubing within the housing configured to deliver a gaseous substance to a user;
    a mouthpiece coupled to the housing and configured to rotate between a first position and a second position; and
    a gasket coupled to the airflow tubing and configured to seal a tube within the mouthpiece in the second position and engage a side of the mouthpiece in the first position, thereby blocking the gaseous substance from escaping the airflow tubing,
    wherein the mouthpiece prevents the gaseous substance from escaping the airflow tubing in the first position and the mouthpiece allows the gaseous substance to escape the airflow tubing in the second position.

13. The vaporizer device of claim 12 wherein the mouthpiece fits within a slot of the housing when in the mouthpiece is in the first position.

14. The vaporizer device of claim 13 wherein the mouthpiece also engages the housing in the first position to prevent the gaseous substance from escaping the airflow tubing or the mouthpiece.

15. A vaporizer device comprising:
- a gasket;
- airflow tubing coupled to the gasket and configured to deliver a gaseous substance to a user;
- a mouthpiece having a tube that extends through the mouthpiece, wherein the mouthpiece is configured to rotate between a first position and a second position; and
- wherein the mouthpiece prevents the gaseous substance from escaping the airflow tubing in the first position by the gasket engaging a side of the mouthpiece, and
- wherein the mouthpiece allows the gaseous substance to escape the airflow tubing in the second position by the gasket creating a seal with the tube.

16. The vaporizer device of claim 15 wherein the mouthpiece comprises a mouthpiece base coupled to the housing and a mouthpiece portion coupled to the mouthpiece base.

17. The vaporizer device of claim 16 wherein the mouthpiece base comprises a bulbous bottom portion and the mouthpiece portion is tapered to form-fit into the mouth piece base.

\* \* \* \* \*